(12) United States Patent  
Everman et al.

(10) Patent No.: US 12,298,295 B2
(45) Date of Patent: May 13, 2025

(54) APPARATUS AND METHOD FOR HUMAN PERFORMANCE EXHALATION SENSING

(71) Applicant: GMECI, LLC, Beavercreek, OH (US)

(72) Inventors: Bradford R. Everman, Haddonfield, NJ (US); Brian Scott Bradke, Brookfield, VT (US)

(*) Notice: Subject to any disclaimer, the term of this patent is extended or adjusted under 35 U.S.C. 154(b) by 0 days.

(21) Appl. No.: 18/524,841

(22) Filed: Nov. 30, 2023

(65) Prior Publication Data

US 2024/0118261 A1    Apr. 11, 2024

Related U.S. Application Data

(63) Continuation of application No. 17/959,521, filed on Oct. 4, 2022, now Pat. No. 11,874,271.

(51) Int. Cl.
| | | |
|---|---|---|
| G01N 33/497 | (2006.01) | |
| G08B 21/18 | (2006.01) | |
| G16H 50/30 | (2018.01) | |

(52) U.S. Cl.
CPC ............ *G01N 33/497* (2013.01); *G16H 50/30* (2018.01); *G01N 33/4975* (2024.05); *G08B 21/182* (2013.01)

(58) Field of Classification Search
CPC .............. G01N 33/497; G01N 33/004; G01N 33/0037; G01N 33/0016; G01N 2033/4975; G01N 2033/4977; G01N 27/4146; G01N 21/766; G01N 21/783; G16H 50/30; G16H 50/20; G16H 50/70; G16H 40/63; G16H 40/67; G16H 40/40; G16H 10/60;

(Continued)

(56) References Cited

U.S. PATENT DOCUMENTS

| | | | | |
|---|---|---|---|---|
| 4,809,810 A | * | 3/1989 | Elfman | G01N 33/4972 |
| | | | | 340/576 |
| 6,656,127 B1 | * | 12/2003 | Ben-Oren | H01J 65/042 |
| | | | | 600/529 |

(Continued)

FOREIGN PATENT DOCUMENTS

| | | | | | |
|---|---|---|---|---|---|
| CA | 3097973 A1 | * | 10/2019 | ........... | A24B 15/167 |
| CA | 3233250 A1 | * | 3/2023 | ............... | A61B 5/08 |
| EP | 4154804 A1 | * | 3/2023 | ............... | A61B 5/08 |
| JP | 4860879 B2 | | 1/2012 | | |
| WO | WO-2017198787 A1 | * | 11/2017 | ........... | A61B 5/0816 |

*Primary Examiner* — Jeffrey P Aiello
(74) *Attorney, Agent, or Firm* — Caldwell Intellectual Property Law

(57) ABSTRACT

An apparatus for human performance exhalation sensing, comprising a housing, wherein the housing comprises an inlet tube configured to receive exhaled gas from an individual, a sensing device positioned within the inlet tube, at least a processor, and a memory communicatively connected to the at least a processor, the memory containing instructions configuring the at least a processor to receive performance data related to at least a task assigned to the individual, generate a performance metric of the individual as a function of the performance data, wherein the performance metric comprises a performance parameter associated with the at least a task, generate a breath profile of the individual as a function of data collected from the exhaled gas, generate a performance determination of the individual as a function of the performance parameter and the breath profile, and alert the individual based on the performance determination.

18 Claims, 7 Drawing Sheets

(58) Field of Classification Search
CPC ........ G16H 20/30; A61B 5/087; A61B 5/082;
A61B 5/0836; A61B 5/097; A61B
5/0816; A61B 5/091; A61B 5/0871; A61B
5/08; A61B 5/7275; A63B 23/18; A63B
2071/0694; A63B 21/00196; G06N 20/00;
G06N 3/08; G01F 1/28
USPC ........ 128/204.22; 422/84, 83, 400; 600/532,
600/529, 538, 531, 323, 301, 484, 533,
600/543, 300; 702/182, 19, 189, 188, 24,
702/183, 104, 45, 127, 1, 23, 50, 139, 55,
702/32, 100
See application file for complete search history.

(56) References Cited

U.S. PATENT DOCUMENTS

| | | | |
|---|---|---|---|
| 9,022,946 B2* | 5/2015 | Haque | A61M 16/0003 600/529 |
| 9,977,865 B1* | 5/2018 | LaBorde | G06K 7/10366 |
| 10,031,126 B2 | 7/2018 | Blake | |
| 10,226,201 B2* | 3/2019 | Ahmad | A61B 10/00 |
| 11,127,272 B2 | 9/2021 | Park | |
| 2018/0369525 A1* | 12/2018 | Buschke | A61M 16/024 |
| 2020/0000369 A1 | 1/2020 | Tiemann | |
| 2020/0337594 A1 | 10/2020 | Reddy | |
| 2021/0316094 A1* | 10/2021 | Kimm | A61M 16/024 |
| 2022/0134030 A1* | 5/2022 | Jenaro | A61M 16/024 128/200.24 |

\* cited by examiner

APPARATUS AND METHOD FOR HUMAN PERFORMANCE EXHALATION SENSING

CROSS-REFERENCE TO RELATED APPLICATIONS

This application is a continuation of Non-provisional Application Ser. No. 17/959,521 filed on Oct. 4, 2022, and entitled "APPARATUS AND METHOD FOR HUMAN PERFORMANCE EXHALATION SENSING," the entirety of which is incorporated herein by reference.

FIELD OF THE INVENTION

The present invention generally relates to the field of sensing devices. In particular, the present invention is directed to an apparatus and method for human performance exhalation sensing.

BACKGROUND

Many data points can be made from gases exhaled from individuals sensed through exhalation sensors. However, the amount of raw data and accuracy of inferences of exhalation sensors can be improved.

SUMMARY OF THE DISCLOSURE

In an aspect, an apparatus for human performance exhalation sensing is described. The apparatus includes a housing, wherein the housing includes an inlet tube configured to receive exhaled gas from an individual, a sensing device positioned within the inlet tube, at least a processor, and a memory communicatively connected to the at least a processor, the memory containing instructions configuring the at least a processor to receive performance data related to at least a task assigned to the individual, generate a performance metric of the individual as a function of the performance data, wherein the performance metric includes a performance parameter associated with the at least a task, generate a breath profile of the individual as a function of data collected from the exhaled gas, generate a performance determination of the individual as a function of the performance parameter and the breath profile, and alert the individual based on the generated performance determination.

In another aspect, a method of using a human performance exhalation sensor is described. The method includes providing an inlet tube to a user, wherein the inlet tube is configured to receive exhaled gas from an individual, receiving, by at least a processor communicatively connected to the sensing device, performance data related to at least a task assigned to the individual, generating a performance metric of the individual as a function of the performance data, wherein the performance metric includes a performance parameter associated with the at least a task, generating, by the at least a processor, a breath profile of the individual as a function of data collected from the exhaled gas, generating, by the at least a processor, a performance determination as a function of the performance parameter and the breath profile, and alerting, by the at least a processor, the individual based on the generated performance determination.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 8 is a block diagram of a computing system that can be used to implement any one or more of the methodologies disclosed herein and any one or more portions thereof.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for human performance exhalation sensing. In an embodiment, an apparatus for human performance exhalation sensing is presented.

Aspects of the present disclosure can be used to provide performance determinations of exhalations of an individual based on breath parameters detected through a sensing device. Aspects of the present disclosure can also be used to improve accuracy of detected breath parameters using machine learning models.

Aspects of the present disclosure allow for determining performances of pilots through breath parameters. Exemplary embodiments illustrating aspects of the present disclosure are described below in the context of several specific examples.

Figure 1:
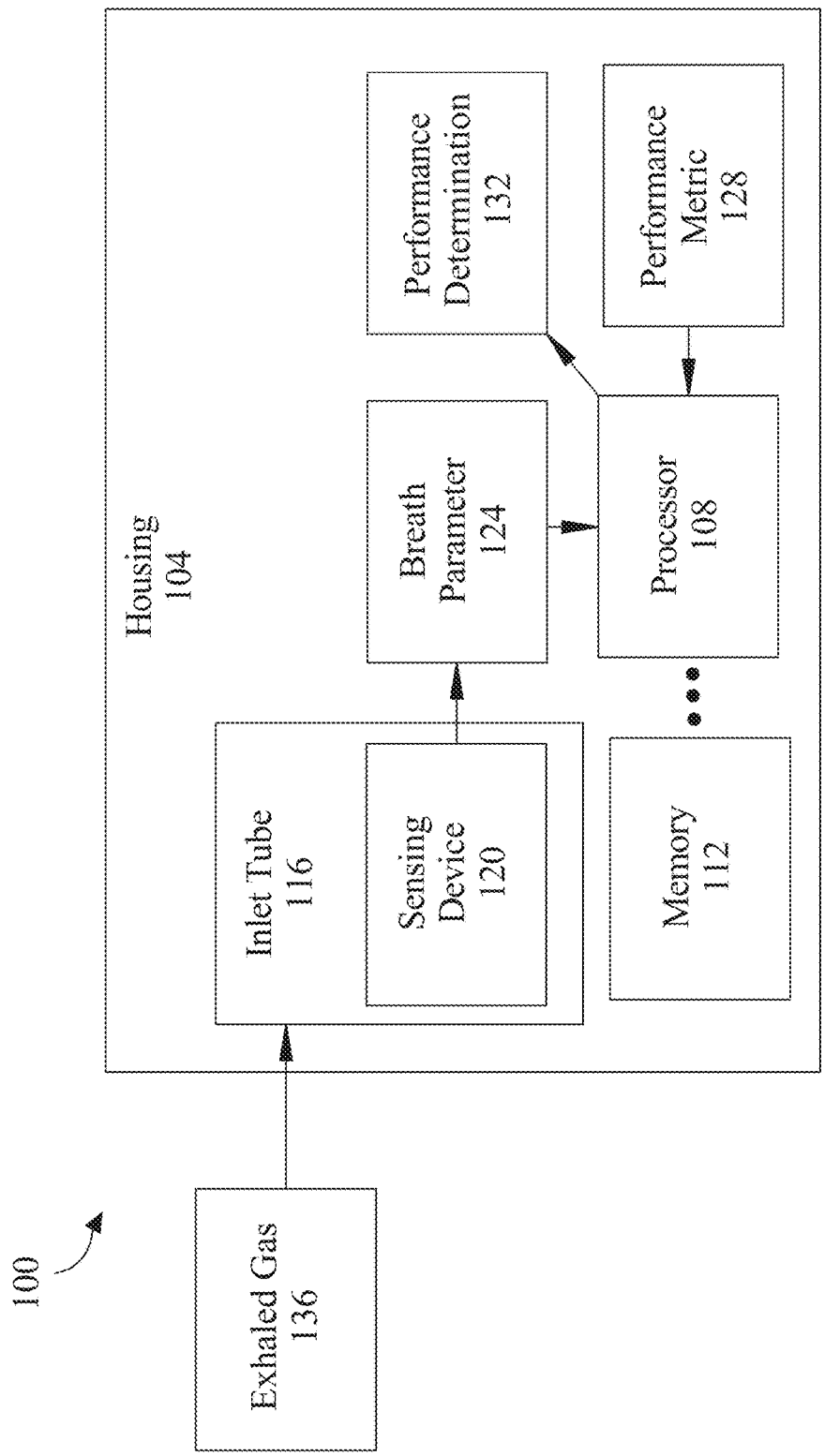
FIG. 1 is an exemplary embodiment of a block diagram of a human performance exhalation sensor.

Referring now to FIG. 1, in some embodiments, apparatus 100 may include a housing 104. A "housing" as used in this disclosure is a structure configured to hold one or more elements. Housing 104 may be constructed of any suitable material or combination of materials, including without limitation metal, metal such as aluminum, titanium, steel, or the like, plant materials including bamboo and/or wood, polymer materials such as polycarbonate, polymethyl methacrylate, acrylonitrile butadiene styrene (ABS), or the like, synthetic fibers such as carbon fiber, silicon carbide fiber, metallic fiber, or the like, composite materials such as fiberglass, laminated fiberglass, plywood, or the like, or any combination of the above. Housing 104 may be manufactured in any suitable process including molding such as injection molding, additive manufacturing such as "three-dimensional printing" and/or stereolithography, subtractive processes such as machining, and/or any other process or combination of processes. Housing 104 may include one or more surfaces. A "surface" as used in this disclosure is a layer of material of an object. Surfaces of housing 104 may include, without limitation, flat surfaces, curved surfaces, angled surfaces, concave surfaces, convex surfaces, and/or any combination thereof. Housing 104 may include two or more surfaces of various compositions, such as, but not limited to, carbon fiber, silicon carbide fiber, metallic fiber, polycarbonate, fiberglass, and the like. In some embodiments, housing 104 may include a rectangular shape, cylindrical shape, square shape, triangle shape, tube shape, and/or any combination thereof. In some embodiments, housing 104 may include a power source. A "power source" as used in this disclosure is an origin of energy. A power source may include, but is not limited to, AC power, DC power, and the like. A power source may include one or more batteries, capacitors, and/or other energy storing devices. In some embodiments, housing 104 may include one or more connections to an external power source.

Referring now to FIG. 1, an exemplary embodiment of apparatus 100 for human performance exhalation sensing is illustrated. In some embodiments, apparatus 100 may include at least a processor 108 and memory 112 communicatively connected to at least a processor 108. Memory 112 may include instructions configuring at least a processor 108 to perform various tasks. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected. For the purposes of this disclosure, elements that are connected by a "communicative connection" are "communicatively connected."

Still referring to FIG. 1, apparatus 100 may include a computing device. Apparatus 100 may include any computing device as described in this disclosure, including without limitation a microcontroller, microprocessor, digital signal processor (DSP) and/or system on a chip (SoC) as described in this disclosure. Apparatus 100 may include, be included in, and/or communicate with a mobile device such as a mobile telephone or smartphone. Apparatus 100 may include a single computing device operating independently, or may include two or more computing device operating in concert, in parallel, sequentially or the like; two or more computing devices may be included together in a single computing device or in two or more computing devices.

Apparatus 100 may interface or communicate with one or more additional devices as described below in further detail via a network interface device. Network interface device may be utilized for connecting apparatus 100 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Apparatus 100 may include but is not limited to, for example, a computing device or cluster of computing devices in a first location and a second computing device or cluster of computing devices in a second location Apparatus 100 may include one or more computing devices dedicated to data storage, security, distribution of traffic for load balancing, and the like. Apparatus 100 may distribute one or more computing tasks as described below across a plurality of computing devices of computing device, which may operate in parallel, in series, redundantly, or in any other manner used for distribution of tasks or memory between computing devices. Apparatus 100 may be implemented using a "shared nothing" architecture in which data is cached at the worker, in an embodiment, this may enable scalability of system 100 and/or computing device.

With continued reference to FIG. 1, apparatus 100 may be designed and/or configured to perform any method, method step, or sequence of method steps in any embodiment described in this disclosure, in any order and with any degree of repetition. For instance, apparatus 100 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Apparatus 100 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, in some embodiments, apparatus 100 may include inlet tube 116. An "inlet tube" as used in this disclosure is a pathway for receiving fluid. Inlet tube 116 may include, without limitation, plastics, carbon fibers, and the like. Inlet tube 116 may include a circular, cylindrical, square, rectangular, and/or other cross-sectional shape. Inlet tube 116 may include a gradient diameter, where a first end of inlet tube 116 may have a larger diameter than a second end of inlet tube 116. In some embodiments, inlet tube 116 may protrude from housing 104. Inlet tube 116 may be part of and/or connected to a face mask, nasal mask, and/or other device. Masks may include, without limitation, a gas mask such as a cannister mask, a self-contained breathing apparatuses (SCBA) such as those used by firefighters, self-contained underwater breathing apparatuses (SCUBA), supplied-air respirators (SAR), particulate respirators, chemical cartridge respirators, powered air-purifying respirators (PAPRs), respirators included as part of a protective suit, airline respirators, N-95 or other NIOSH approved respirators, and/or other devices worn on and/or over and at least partially occluding the face to aid in respiration. In some embodiments, inlet tube 116 may be part of and/or connected to a mobile respiratory device. A "mobile respiratory device," as used herein, is a device worn on or about a face of a person, which aids in respiration, for instance when the person is in an environment where oxygen may be scarce or where other gases or particular matter such as carbon dioxide, carbon dioxide, toxic gases, droplets or fumes, or other elements that may interfere with respiration, and/or gases having ambient temperatures capable of harming a person when inhaled. Such an environment may include, without limitation, a cockpit of an aircraft such as a military aircraft, an artificially or naturally formed tunnel with an atmosphere that makes breathing difficult, such as an anoxic atmosphere, an atmosphere containing poisonous or otherwise problematic gases such as sulfur dioxide, carbon dioxide, carbon monoxide, or the like, a location at a high altitude such as a mountaintop, a location of a chemical spill, and the like.

Still referring to FIG. 1, in some embodiments, housing 104 may include an exhaust port. An "exhaust port," as used in this disclosure, is an outlet that permits air exhaled by a user to escape from inlet tube 116 and/or housing 104. In some cases, a "user" may be referred to as an "individual." An exhaust port may include a valve such as a check-valve or other one-way valve to prevent air from entering a housing 104 from an environment. An exhaust port may include, for instance, an exhale valve of a respirator mask or other such design. An exhaust port may also be an inlet port; for instance, air may be filtered while breathing in through the port and then exhaled, with or without filtering, via a valve at the same port.

Still referring to FIG. 1, in some embodiments, apparatus 100 may include a sensing device 120. Sensing device 120 may be positioned within inlet tube 116, such as, without limitation on an interior surface of inlet tube 116. In some embodiments, sensing device 120 may be in fluid communication with inlet tube 116. A "sensing device" as used in this disclosure is a device capable of detecting elements of the physical world. Sensing device 120 is configured to detect one or more quantities and/or percentages of gases. In an embodiment, sensing device 120 is configured to detect a carbon dioxide level and generate sensing device 120 outputs indicating detected carbon dioxide level. Sensing device 120 may alternatively or additionally detect one or more gases, droplets, particulate elements, or the like, which may be indicative of health and/or physiological status of a person using inlet tube 116 and/or apparatus 100, of environmental conditions that may affect such status, or both. Sensing device 120 may be configured to detect a carbon dioxide level by detecting a level of a related compound detecting the carbon dioxide level as a function of the level of the related compound. A "related compound," as used in this disclosure, is a compound, quantities, percentages, and/or concentrations of which may be used to predict quantities, percentages, and/or concentrations of carbon dioxide in one or more contexts, owing to statistical correlations between the two. For instance, and without limitation, quantities, percentages, and/or concentrations of carbon dioxide from sources such as humans and/or other animals may be proportional to quantities, percentages, and/or concentrations of $H_2$ (hydrogen) gas and/or volatile organic compounds. In an embodiment, a related compound may be more readily or accurately detected using an electrical component of a sensing device 120. Sensing device 120 may detect a quantity, percentage, and/or concentration of a related compound such as $H_2$, volatile organic compounds, or the like and calculating an associated level of $CO_2$. Sensing device 120 may be configured to detect quantities, percentages, and/or concentrations of any other compound directly and/or by detection of a related compound and calculation of the quantities, percentages, and/or concentrations. Such a signal may be used to distinguish the influence of a human presence from other contaminants; for instance, in indoor environments, $H_2$ concentration may be related to $CO_2$ concentration as human breath contains significant concentrations of both, $CO_2$ (4%) and $H_2$ (10 ppm).

Still referring to FIG. 1, sensing device 120 may be configured to detect quantities, percentages, and/or concentrations of hydrogen gas ($H_2$). Sensing device 120 may be configured to sense quantities, percentages, and/or concentrations of one or more volatile organic compounds. A "volatile organic compound," as used in this disclosure, are organic compounds having high vapor pressure at room temperature. Volatile organic compounds may include without limitation, alcohols such as ethanol, isoprene, chlorofluorocarbons, benzine, methylene chloride, perchloroethylene, methyl tert-butyl ether (MTBE), and/or formaldehyde. Sensing device 120 may be configured to detect a total volatile organic compound (tVOC) quantities, percentage, and/or concentration. "Total volatile organic compound," as used in this disclosure, is a total concentration of volatile organic compounds present simultaneously in the air. Sensing device 120 may detect tVOC using a sensing device 120 that is sensitive to sets of volatile organic compounds, a sensing device 120 that is sensitive to each of a plurality of volatile organic compounds, and/or sensitive to one or more organic compounds having a quantities, percentages, and/or concentrations of which may be used to predict quantities, percentages, and/or concentrations of tVOC and/or components thereof. For instance, and without limitation, quantities, percentages, and/or concentrations of ethanol in air may be associated with quantities, percentages, and/or concentrations of other volatile organic compounds; sensing device 120 may be configured to detect levels and/or quantities of ethanol and calculate tVOC using such detected quantities.

With continued reference to FIG. 1, sensing device 120 may alternatively or additionally be configured to sense one or more hazardous gases, droplets, particulate matter or the like, including without limitation hazardous gases, droplets, particulate matter produced by indoor or outdoor air pollution sources, whether natural or anthropogenic, hazardous gases, droplets, particulate matter produced intentionally as an act of violence or war, or the like. Alternatively or additionally, sensing device 120 may be configured to detect one or more diagnostically useful gases, droplets, particulate matter or the like, where a "diagnostically useful" gas, droplet, and/or element of particulate matter is defined as a gas, droplet, and/or element of particulate matter that provides information usable to determine a physiological state of a user, for instance as described in further detail below.

Still referring to FIG. 1, sensing device 120 may function using any suitable technology, including without limitation a detector, defined as a circuit element that modifies a circuit parameter when exposed to a compound to be detected. For instance, and without limitation, sensing device 120 may use a heating element to temperature of a heated metal-oxide detector, such as a tin-based component that changes resistance based on exposure to a compound to be detected; output may be fed to an operational amplifier, such as without limitation an operational amplifier configured to cover a measurement range of 8 orders of magnitude. Sensing device 120 may include, for instance, a first such detector configured to detect $CO_2$ and/or a related compound and a second detector configured to detect tVOC and/or a representative compound such as ethanol as described above. Sensing device 120 may include, without limitation, input and output ports, a microcontroller for performing calculations as described above, one or more registers and/or more memory elements such as without limitation random-access memory (RAM) such as block random-access memory (BRAM), flash memory, or the like. Sensing device 120 may include one or more wireless transceivers or other devices for communication with other elements of apparatus 100, and/or may be wired to such elements. Sensing device 120 may be connected to a power source such as a battery or other voltage source.

Alternatively or additionally, and still referring to FIG. 1, sensing device 120 may include one or more sensors and/or detectors operating according to one or more additional technologies, such as without limitation at least a chemical sensing device, which may be based on polymer or heteropolysiloxane; a chemical sensing device may be configured to detect concentrations of $CO_2$, estimated $CO_2$, tVOC, and/or any other element that may be detected by sensing device 120 as above.

Still referring to FIG. 1, sensing device 120 may be configured to generate breath parameter 124. A "breath parameter" as used in this disclosure is a metric pertaining to gases from lungs of a user. Breath parameter 124 may include, without limitation, oxygenation values, respiration rates, respiration intensity, and the like. "Oxygenation values" as used in this disclosure are metrics pertaining to a concentration of oxygen of a fluid. Sensing device 120 may be configured to determine breath parameter 124 from exhaled gas 136. "Exhaled gas" as used in this discourse is a breath of a user. A user may provide exhaled gas 136 through inlet tube 116. Sensing device 120 may determine one or more breath parameters 124 of exhaled gas 136. Breath parameters 124 may include, without limitation, levels and/or frequencies of one or more volatile organic compounds (VOCs). VOCs may include, without limitation, isoprene, terpenes, pinene isomers, sesquiterpenes, methanol, and the like. Sensing device 120 may be configured to detect breath parameter 124 during timed intervals, such as, but not limited to, 10 seconds, 30 seconds, one minute, and the like.

Still referring to FIG. 1, in some embodiments, sensing device 120 may be communicatively connected to at least a processor 108. At least a processor 108, also referred to as "processor 108", may be configured to receive breath parameter 124. Processor 108 may be configured to generate and/or receive performance metric 128. A "performance metric" as used in this disclosure is a value pertaining to a scored outcome of an event. A scored outcome may include a value showing a competency of a performed task. Performance metric 128 may include one or more values of, but not limited to, respiration rates, chemical compositions, respiration volumes, and the like. Processor 108 may use a performance metric machine learning model to determine performance metric 128. A performance metric machine learning model may be trained with training data correlating breath parameters and/or user profiles to performance metrics. Training data may be received from user input, external computing devices, and/or previous iterations of processing, without limitation. A performance metric machine learning model may be configured to input user profiles and/or breath parameter 124 and generate performance metric 128. As a non-limiting example, a performance machine learning model may receive as input breath parameter 124 of a respiration rate and generate performance metric 128 to include a respiration rate of 12 breaths a minute. In some embodiments, performance metric 128 may be communicated to processor 108 through an external computing device, user input, and the like, without limitation.

Still referring to FIG. 1, in some embodiments, performance metric 128 may be correlated by processor 108 to performance data of a user. "Performance data" as used in this disclosure is one or more metrics of completion of one or more tasks. Tasks may include, without limitation, one or more operations of flying a plane, such as turning, braking, accelerating, liftoff, landing, and the like. Performance data may include, without limitation, angles of turns, velocities, accelerations, projected flight paths, turning speeds, degrees of rotation, and the like.

Still referring to FIG. 1, in some embodiments, apparatus 100 may determine performance determination 132 as a function of one or more performance parameters. In some embodiments, processor 108 may compare breath parameter 124 to performance metric 128 to generate performance determination 132. Processor 108 may compare breath parameter 124 to one or more performance parameters. A "performance parameter" as used in this disclosure is a metric pertaining to a task. Tasks may include, but are not limited to, operating cars, planes, boats, motorcycles, and the like. In some embodiments, a task may include operating a fighter pilot jet. Tasks may include one or more subtasks. A "subtask" as used in this disclosure is a portion of an objective. Subtasks may include, but are not limited to, pre-flight checks, starting engines, engaging safety equipment, performing a turn of a vehicle, halting a motion of a vehicle, and the like. Processor 108 may classify and/or categorize tasks and/or subtasks to one or more task categories. A "task category" as used in this disclosure is a classification of a task to a group. Task categories may include, but are not limited to, operations of one or more vehicles, such as turning, braking, accelerating, pivoting, diving, climbing, reversing, and the like. Processor 108 may classify subtasks to one or more subtask groupings. Subtask groupings may include, but are not limited to, pre-flight checks, engaging safety equipment, and the like.

Still referring to FIG. 1, a performance parameter may include, without limitation, interaction with one or more pilot controls of a plane. Interaction with one or more pilot controls of a plane may include, without limitation, turning, braking, liftoff, landing, climbing, cruising, and the like. In some embodiments, performance parameter may include an operating posture of an individual. An operating posture of an individual may include, without limitation, a spine alignment, head tilt, arm and/or shoulder placement, and the like. In some embodiments, performance parameter may include one or more biological performances of an individual. A "biological performance" as used in this disclosure is a score of a vital sign corresponding to a task. Biological performances may include, without limitation, eye movements of an individual, heart rates, heart rhythms, breathing rates, skin temperatures, skin conductivities, and the like. For instance, and without limitation, a biological performance may include an oxygenation of an individual's blood while experiencing intense gravitational forces (G forces), such as 8 G's.

Still referring to FIG. 1, a performance parameter may be determined through user input and/or one or more external computing devices, without limitation. In some embodiments, performance parameter may be determined through a machine learning model, such as any machine learning model as described throughout this disclosure, without limitation. In some embodiments, processor 108 may categorize performance data to one or more performance parameters. Processor 108 may utilize a performance parameter classifier. A performance parameter classifier may be trained with training data categorizing performance data to performance parameters such as, but not limited to, eye movements, postures, hand placements, breathing rates, and the like. Training data may be received through user input, external computing devices, and/or previous iterations of processing. In some embodiments, a performance parameter classifier may be configured to input performance data and output one or more classifications of performance data to one or more performance parameters. As a non-limiting example, sensing device 120 may include a camera and performance data may include eye movements of an individual. A performance parameter classifier may classify the eye movements to category of task focusing. A performance parameter classifier may be used by processor 108 to parse performance data into performance parameter categories, which may allow faster and/or more accurate generation of performance determination 132.

Still referring to FIG. 1, in some embodiments, processor 108 may generate a performance determination machine learning model. A "performance determination machine learning model" as used in this disclosure is a machine learning process that outputs performance determinations. A performance determination machine learning model may be trained with training data correlating breath parameters and/or performance data to performance determinations 132. Training data may be received from user input, external computing devices, and/or previous iterations of processing. In some embodiments, a performance determination machine learning model may be configured to receive as input breath parameter 124 and output performance determinations 132. Performance determinations 132 may include one or more values associated with one or more parts of a task. In some embodiments, performance determinations 132 may include scores out of 10, percentages out of 100, words and/or phrases, and the like, without limitation. For instance and without limitation, performance determination 132 may include a score of "adequate" of a task of operating an airplane in cruise mode. In some embodiments, a performance determination machine learning model may generate performance determination 132 with a temporal element. A "temporal element" as used in this disclosure is any metric associated with time. A temporal element may include, but is not limited to, microseconds, seconds, minutes, hours, days, and the like. A performance determination machine learning model may provide performance determinations 132 corresponding to temporal elements of a task. For instance, and without limitation, a performance determination machine learning model may provide performance determination 132 of 70% at Sep. 20, 2022, 12:26:54 PM of an individual performing a pre-flight check of an aircraft. A performance determination machine learning model may update performance determinations 132 in real time. "Real time" as used in this disclosure is the actual time during which a process or event occurs. Continuing the above example, a performance determination machine learning model may update performance determination 132 from 70% to 77% at Sep. 20, 2022, 12:27:04 PM of an individual performing a pre-flight check of an aircraft. A performance determination machine learning model may provide one or more timestamps with one or more performance determinations 132. A "time stamp" as used in this disclosure is a flagged temporal element. A time stamp may include a precise time, range of times, and the like. For instance and without limitation, a performance determination machine learning model may output a first performance determination 132 of 8 out of 10 at a first given time and a second performance determination 132 of 9 out of 10 at a second given time. Processor 108 and/or a performance determination machine learning model may generate a performance timeline. A "performance timeline" as used in this disclosure is a set of one or more points in time associated with a performance of a task. A performance timeline may include, but is not limited to, a single task, a plurality of tasks, a combination of tasks through a day, a combination of tasks throughout a week, and the like.

Still referring to FIG. 1, in some embodiments, processor 108 and/or a performance determination machine learning model may be additionally configured to determine a confidence metric associated with correlations and/or determinations. As used in this disclosure, a "confidence metric" is a quantified expression of confidence associated with a function, such as a likelihood or probability that an output of a function is accurate or correct. Determination of a confidence metric may include any appropriate process described in this disclosure. In some cases, a confidence metric may be a proportional or unitless figure, for example expressed in terms of a proportion or percentage. Alternatively of additionally, a confidence metric may be represented using relative or absolute units. In some cases, a confidence metric may be compared to a threshold confidence metric in order to determine suitability of an associated correlation and/or determination, for example of a cognitive status. For instance, in some cases a confidence metric no less than a threshold confidence metric of 95%, 90%, 85%, 75%, or 50% is required in order to assure an underlying correlation and/or determination of breath parameter 124 is "correct."

Still referring to FIG. 1, in some embodiments, processor 108 may generate a performance classifier. A "performance classifier" as used in this disclosure is a machine learning process that categorizes input data to performance categories. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Processor 108 and/or another device may generate a classifier using a classification algorithm, defined as a processes whereby processor 108 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, processor 108 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Processor 108 may then calculate a likelihood table by calculating probabilities of different data entries and classification labels. Processor 108 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, processor 108 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, a performance classifier may be trained with training data correlating performance data and/or performance determinations to categories of performances. Training data may be received through user input, external computing devices, and/or previous iterations of processing. In some embodiments, a performance classifier may be configured to input performance parameters, performance data, and/or performance determinations 128, and output one or more performance categories. In some embodiments, processor 108 may be configured to categorize performance data to one or more performance categories. A "performance category" as used in this disclosure is a classification of data to a competency element. Processor 108 may utilize a performance classifier, and/or other machine learning process, without limitation, to classify performance data to performance categories, such as, but not limited to, physiological parameters. Physiological parameters may include, but are not limited to, hear rates, breathing rates, skin temperatures, eye movements, speech patterns, and the like.

Still referring to FIG. 1, in some embodiments, processor 108 may use a breath parameter machine learning model to determine one or more breath parameters 124 and/or performance determinations 128. A breath parameter machine learning model may be trained with training data correlating breath parameters to performance determinations. In some embodiments, a breath parameter machine learning model may be trained with training data correlating exhaled gas 136 to one or more breath parameters 124. Training data may be received from user input, external computing devices, and/or previous iterations of processing. Processor 108 may use a breath parameter machine learning model to determine breath parameter 124 from exhaled gas 136. For instance, and without limitation, processor 108 may input data from exhaled gas 136 into a breath parameter machine learning model, to which the breath parameter machine learning model may output breath parameter 124 of an oxygenation value of exhaled gas 136. Data of exhaled gas 136 may include, without limitation, air pressure, lung volume, identification of a user emitting exhaled gas 136, and the like. In some embodiments, processor 108 may use a breath parameter machine learning model to determine performance determination 132. For instance, and without limitation, processor 108 may input exhaled gas 136 and/ore breath parameter 124 and output performance determination 132, where performance determination 132 shows a score of 9 out of 10 for a respiration rate. Processor 108 may train any machine learning model locally and/or receive a trained machine learning model from one or more external computing devices, without limitation. In some embodiments, processor 108 may communicate with a cloud-based network. A "cloud-based network" as used in this disclosure is a group of two or more computing devices communicating remotely. Processor 108 may communicate any data and/or receive any data through a cloud-based network. In some embodiments, a cloud-based network may communicate a machine learning and/or parameters of a machine learning model to processor 108. Processor 108 may offload one or more computing tasks to a cloud-based network.

Still referring to FIG. 1, in some embodiments, breath parameter 124, performance determination 132, and/or performance metric 128 may be stored in one or more databases. A database may be implemented, without limitation, as a relational database, a key-value retrieval database such as a NOSQL database, or any other format or structure for use as a database that a person skilled in the art would recognize as suitable upon review of the entirety of this disclosure. A database may alternatively or additionally be implemented using a distributed data storage protocol and/or data structure, such as a distributed hash table or the like. A database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Still referring to FIG. 1, in some embodiments, processor 108 may be configured to operably switch sensing device 120 between a performance analysis mode and a passive analysis mode. A "performance analysis mode" as used in this disclosure is an operation state in which one or more sensing devices and/or processors operate at an enhanced level. An "enhanced level" as used in this disclosure is an operation state having a faster processing time. A performance analysis mode may include, but is not limited to, faster processing times, increased sensitivity levels of sensing device 120, higher frequency of sensing rates of sensing device 120, and the like. For instance, and without limitation, a performance analysis mode may include a sampling rate of sensing device 120 of 200 Hz. A "passive analysis mode" as used in this disclosure is a processing state at which one or more processors and/or sensing devices operate at a lower power level. A passive analysis mode may include, but is not limited to, limited processing speed, lower sample rates, lower power consumption, and the like. For instance, and without limitation, a passive analysis mode may include a sampling rate of sensing device 120 of 60 Hz. Processor 108 may switch between analysis modes based on a fuzzy inference engine, fuzzy logic comparison, and the like, as described in FIG. 5 below.

Still referring to FIG. 1, in some embodiments, housing 104 may include a display device. A "display device" as used in this disclosure is an electronic component having a screen. A display device may include, but is not limited to, an LCD screen, OLED screen, and/or other display device. In some embodiments, a display device of housing 104 may be positioned on an exterior surface of housing 104. A display device may be in electronic communication with processor 108. "Electronic communication" as used in this disclosure is a data connection. Electronic communication may include, but is not limited to, wired connections, wireless connections, and the like, without limitation. Processor 108 may be configured to display performance determination 132, breath parameter 124, and the like, to a user through a display device. A display device may include, but is not limited to, monitors, laptops, smartphones, HUD displays, augmented reality (AR) devices, and the like. In some embodiments, processor 108 may display any data as described above through a graphical user interface (GUI) of display device 136. A "graphical user interface" as used in this disclosure is a collection of interactive pictorial icons displayed on a screen. A GUI may include, without limitation, one or more graphics, animations, fonts, and the like. In some embodiments, processor 108 may display any data as described throughout this disclosure in real time through display device 136.

Still referring to FIG. 1, in some embodiments, processor 108 may generate a breath profile of an individual. A "breath profile" as used in this disclosure is a collection of data relating to exhaled gas of a user. A breath profile may include, without limitation, exhalation rates, exhalations chemical composition, breath parameters, performance determinations corresponding to the breath parameters, and the like. Processor 108 may utilize a breath profile of an individual to tune breath parameter 124, performance metric 128, and/or performance determination 132. For instance, and without limitation, a user may have a breath profile showing they tend to naturally have an elevated temperature of exhaled gas. Processor 108 may compensate for an elevated temperature of exhaled gas through adjusting performance metric 128. A breath profile may be stored in a database. Database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Still referring to FIG. 1, in some embodiments, processor 108 may be configured to generate an alert as a function of breath parameter 124. An alert may include, but is not limited to, LED flashes, audible outputs, vibratory outputs, and the like. In some embodiments, housing 104 may include one or more speakers, LEDs, vibratory devices, and the like. Processor 108 may activate a speaker of hosing 104 as a function of breath parameter 124 to alert a user of one or more metrics of breath parameter 124.

Figure 2:
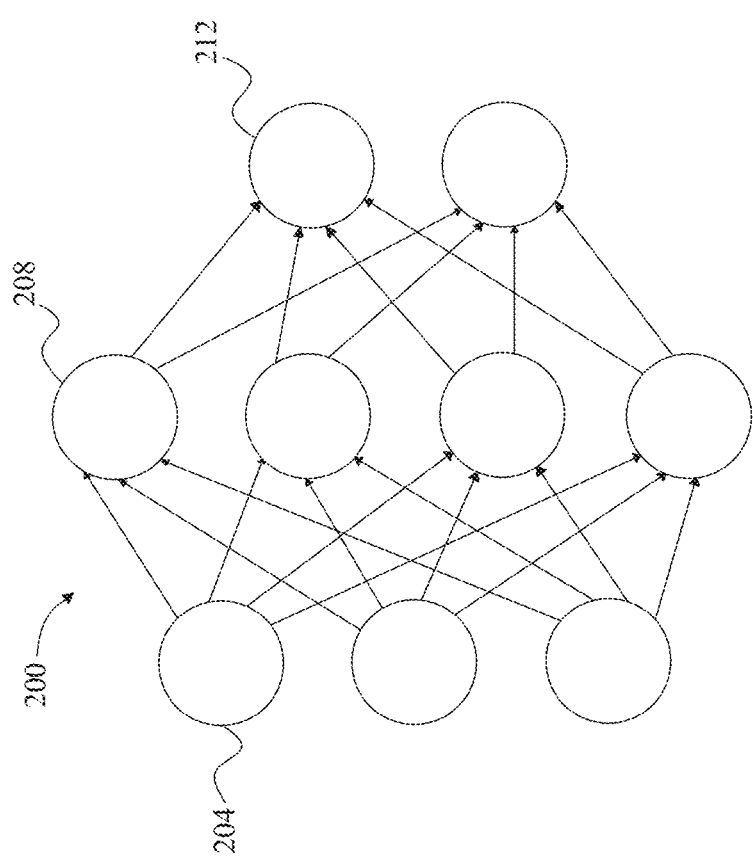
FIG. 2 is an exemplary embodiment of a neural network.

Referring now to FIG. 2, an exemplary embodiment of neural network 200 is illustrated. A neural network 200 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 204, one or more intermediate layers 208, and an output layer of nodes 212. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 3:
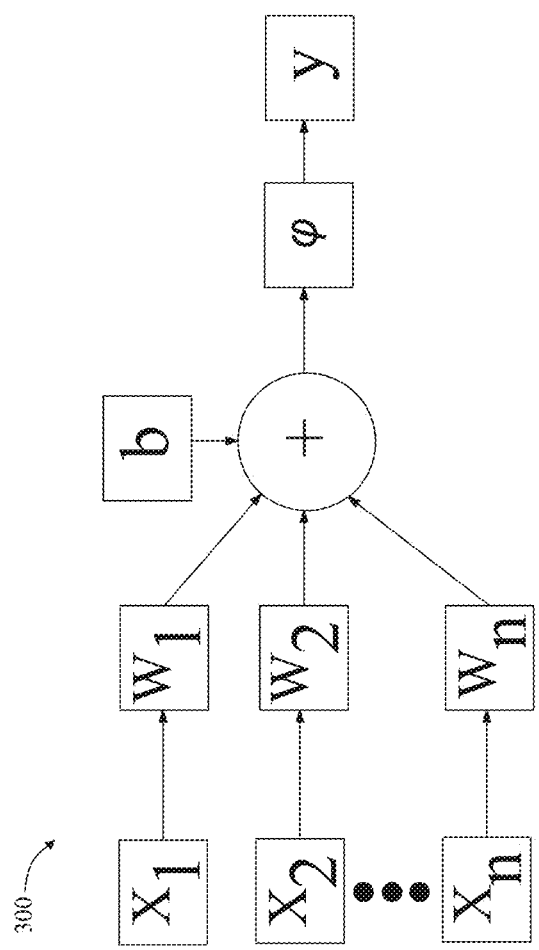
FIG. 3 is an exemplary embodiment of a node of a neural network.

Referring now to FIG. 3, an exemplary embodiment of a node of a neural network is illustrated. A node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 4B:
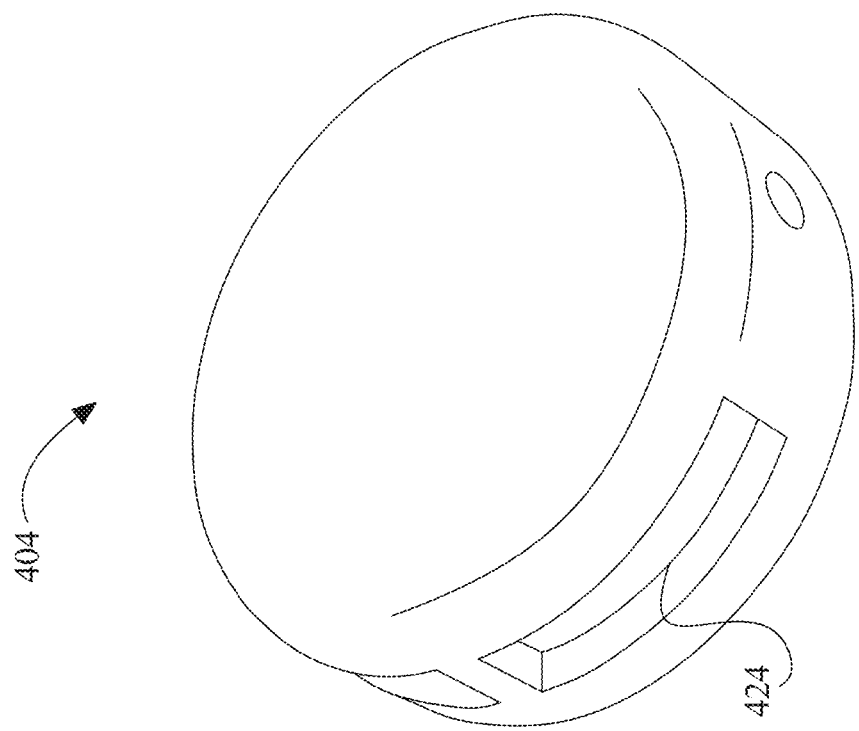
FIGS. 4A and 4B are exemplary embodiments of a housing for a human performance exhalation sensor.
Figure 4A:
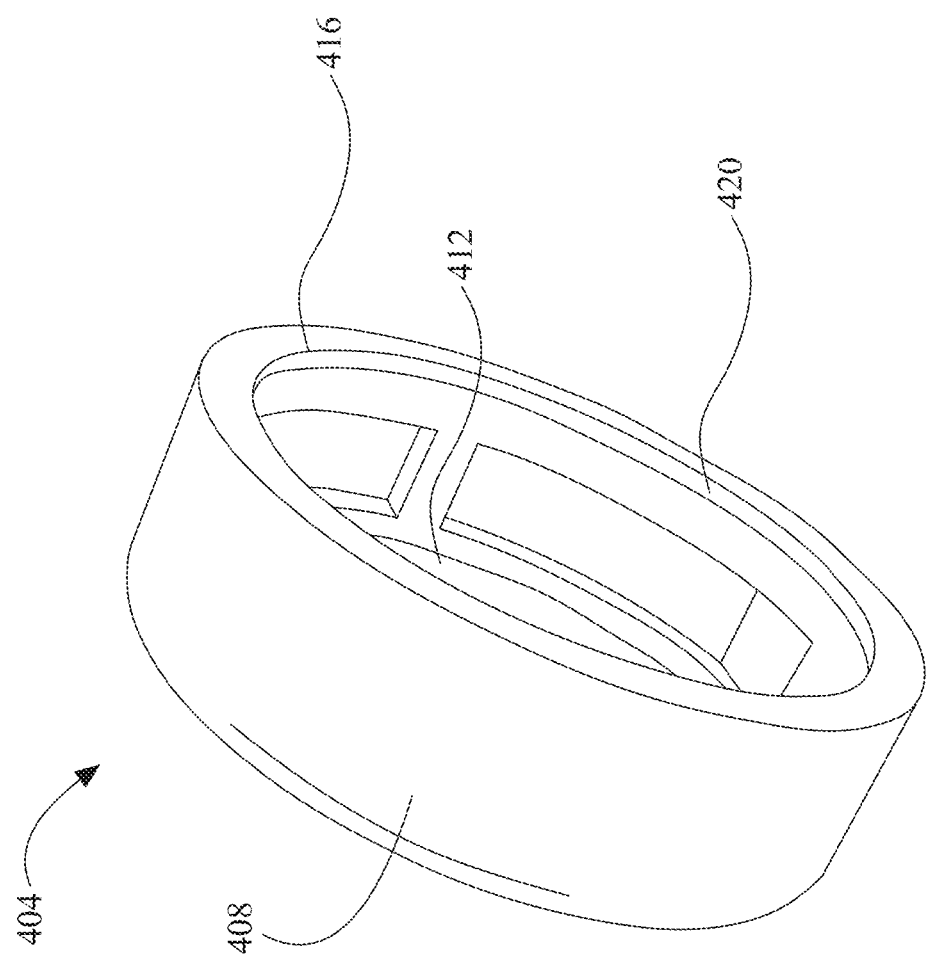

Referring now to FIG. 4A, a perspective view of an exemplary embodiment of a housing 404 is illustrated. Housing 404 may include an exterior surface 408, an interior surface 412, an interior space surrounded by interior surface 412, and one or more apertures. Housing 404 may have any suitable shape, including a shape of a cap to be placed over a respiratory exhaust port as described in further detail below. Housing 404 may be substantially cylindrical and may have one or more rounded edges. Housing 404 may include a port aperture 416. A "port aperture" as used in this disclosure is a hole that receives exhaled breath. Port aperture 416 may include an aperture that receives exhaled breath from a respiratory exhaust port as described in further detail below, admitting the exhaled breath into interior space of housing 404. Housing 404 further includes a connector 420, which may be located at port aperture 416. A "connector," as used in this disclosure, is a structural feature and/or component that affixes one aperture, opening, port, or the like to another in a way that permits flow of fluids such as liquid and/or gases to flow from one aperture, opening, port, or the like to another. Connector 420 may be configured to attach port aperture 416 to exhaust port. Connector 420 may include, without limitation, a rim that fits and/or snaps over a feature of exhaust port to affix port aperture 416 thereto; connector 420 may alternatively or additionally include fastener, such as a bold or screw that inserts through a hole in housing 404 and screws into a reciprocally threaded hole in exhaust port. Connector 420 may include threading around port aperture 416 that engages reciprocal threading at exhaust port. Connector 420 may include and/or be combined with adhesives, sealants, or the like. Connector 420 may permit repeated detachment and reattachment or may effect a permanent connection between port aperture 416 and exhaust port. Persons skilled in the art, upon reviewing the entirety of this disclosure, will be aware of various alternative or additional structures and/or components that may be used for connector 420. Port aperture 208 may be located opposite a sensor-bearing surface; for instance, a sensor-bearing surface may be located on interior surface 412 at a distal end of housing 404, while port aperture 416 may be located at a proximal end of housing 404.

Referring now to FIG. 4B, housing 404 may include at least an ambient aperture 424 connecting to an exterior environment. An "exterior environment," as used in this disclosure, means air that is exterior to an element of mobile respiratory equipment as described below; for instance, where mobile respiratory equipment is a respirator mask, exterior environment may include air outside of the mask and around a person wearing the mask, as opposed to air or gas between the mask and mouth or nose of the person. At least an ambient aperture 424 includes an opening connecting interior space to exterior environment. At least an ambient aperture 424 may permit air to travel freely between interior space and exterior environment.

Figure 5:
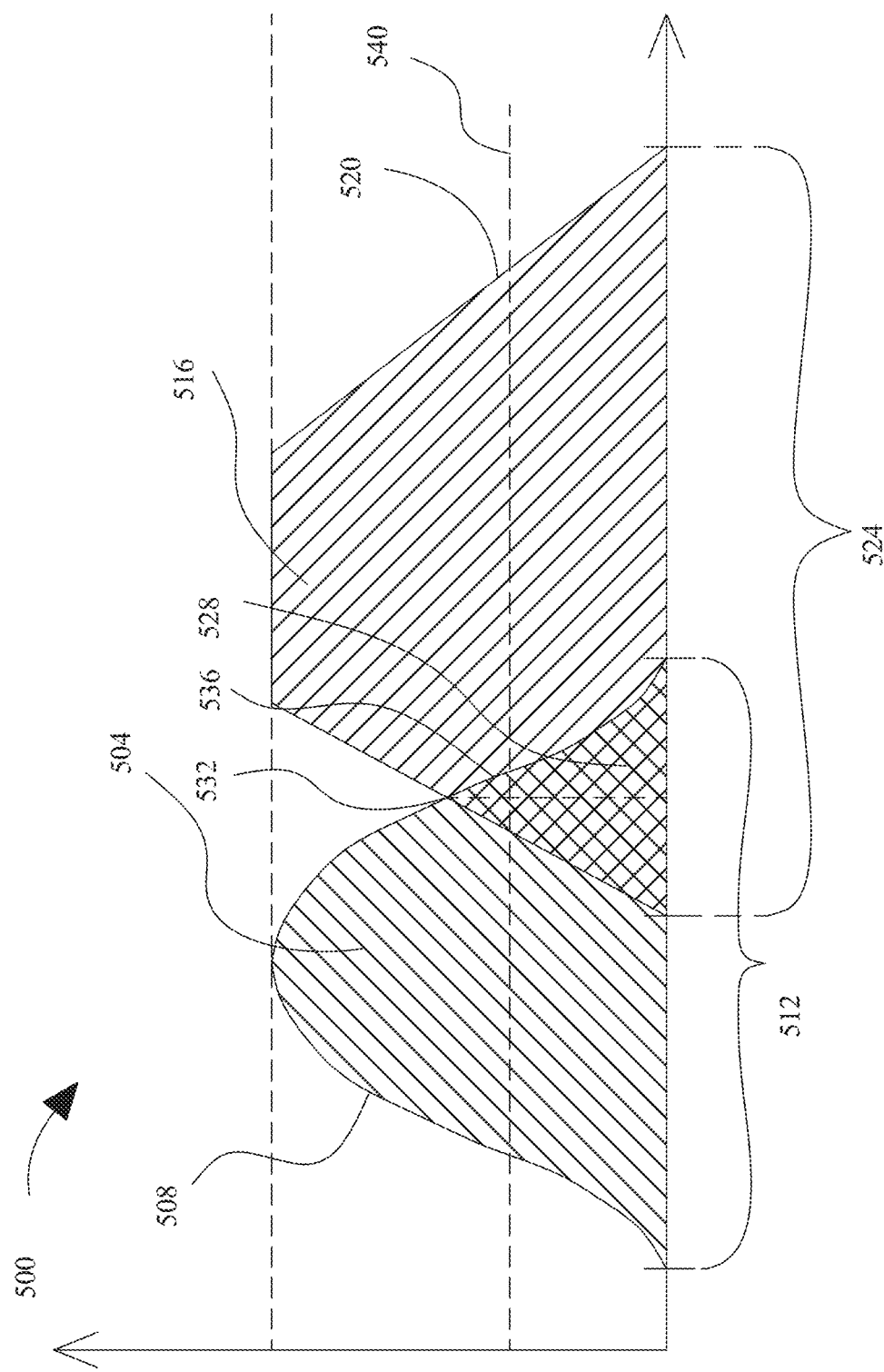
FIG. 5 is a diagram of an exemplary embodiment of a fuzzy logic comparison.

Referring to FIG. 5, an exemplary embodiment of fuzzy set comparison 500 is illustrated. A first fuzzy set 504 may be represented, without limitation, according to a first membership function 508 representing a probability that an input falling on a first range of values 512 is a member of the first fuzzy set 504, where the first membership function 508 has values on a range of probabilities such as without limitation the interval [0,1], and an area beneath the first membership function 508 may represent a set of values within first fuzzy set 504. Although first range of values 512 is illustrated for clarity in this exemplary depiction as a range on a single number line or axis, first range of values 512 may be defined on two or more dimensions, representing, for instance, a Cartesian product between a plurality of ranges, curves, axes, spaces, dimensions, or the like. First membership function 508 may include any suitable function mapping first range 512 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, & \text{for } x > c \text{ and } x < a \\ \frac{x-a}{b-a}, & \text{for } a \leq x < b \\ \frac{c-x}{c-b}, & \text{if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}(\frac{x-c}{\sigma})^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 5, first fuzzy set 504 may represent any value or combination of values as described above, including output from one or more machine-learning models, breath parameters, and a predetermined class, such as without limitation of performance determinations. A second fuzzy set 516, which may represent any value which may be represented by first fuzzy set 504, may be defined by a second membership function 520 on a second range 524; second range 524 may be identical and/or overlap with first range 512 and/or may be combined with first range via Cartesian product or the like to generate a mapping permitting evaluation overlap of first fuzzy set 504 and second fuzzy set 516. Where first fuzzy set 504 and second fuzzy set 516 have a region 528 that overlaps, first membership function 508 and second membership function 520 may intersect at a point 532 representing a probability, as defined on probability interval, of a match between first fuzzy set 504 and second fuzzy set 516. Alternatively or additionally, a single value of first and/or second fuzzy set may be located at a locus 536 on first range 512 and/or second range 524, where a probability of membership may be taken by evaluation of first membership function 508 and/or second membership function 520 at that range point. A probability at 528 and/or 532 may be compared to a threshold 540 to determine whether a positive match is indicated. Threshold 540 may, in a non-limiting example, represent a degree of match between first fuzzy set 504 and second fuzzy set 516, and/or single values therein with each other or with either set, which is sufficient for purposes of the matching process; for instance, threshold may indicate a sufficient degree of overlap between an output from one or more machine-learning models and/or breath parameters and a predetermined class, such as without limitation performance determinations categorization, for combination to occur as described above. Alternatively or additionally, each threshold may be tuned by a machine-learning and/or statistical process, for instance and without limitation as described in further detail below.

Further referring to FIG. 5, in an embodiment, a degree of match between fuzzy sets may be used to classify a breath parameter with performance determinations. For instance, if a performance determination has a fuzzy set matching breath parameters fuzzy set by having a degree of overlap exceeding a threshold, processor 108 may classify the breath parameters as belonging to the performance determination categorization. Where multiple fuzzy matches are performed, degrees of match for each respective fuzzy set may be computed and aggregated through, for instance, addition, averaging, or the like, to determine an overall degree of match.

Still referring to FIG. 5, in an embodiment, breath parameters may be compared to multiple performance determination categorization fuzzy sets. For instance, breath parameters may be represented by a fuzzy set that is compared to each of the multiple performance determination categorization fuzzy sets; and a degree of overlap exceeding a threshold between the breath parameters fuzzy set and any of the multiple performance determination categorization fuzzy sets may cause processor 108 to classify the breath parameters as belonging to performance determination categorization. For instance, in one embodiment there may be two performance determination categorization fuzzy sets, representing respectively performance determination categorization and a performance determination categorization. First performance determination categorization may have a first fuzzy set; Second performance determination categorization may have a second fuzzy set; and breath parameters may have a breath parameters fuzzy set. Processor 108 for example, may compare a breath parameters fuzzy set with each of performance determination categorization fuzzy set and in a performance determination categorization fuzzy set, as described above, and classify a breath parameters to either, both, or neither of performance determination categorization or in a performance determination categorization. Machine-learning methods as described throughout may, in a non-limiting example, generate coefficients used in fuzzy set equations as described above, such as without limitation x, c, and σ of a Gaussian set as described above, as outputs of machine-learning methods. Likewise, breath parameters may be used indirectly to determine a fuzzy set, as breath parameters fuzzy set may be derived from outputs of one or more machine-learning models that take the breath parameters directly or indirectly as inputs.

Still referring to FIG. 5, a computing device may use a logic comparison program, such as, but not limited to, a fuzzy logic model to determine a performance determination score. A performance determination score may include, but is not limited to, amateur, average, good, superior, and the like; each such performance determination score may be represented as a value for a linguistic variable representing performance determination score or in other words a fuzzy set as described above that corresponds to a degree of competency, as calculated using any statistical, machine-learning, or other method that may occur to a person skilled in the art upon reviewing the entirety of this disclosure. In other words, a given element of breath parameters may have a first non-zero value for membership in a first linguistic variable value such as "1" and a second non-zero value for membership in a second linguistic variable value such as "2." In some embodiments, determining a performance determination categorization may include using a linear regression model. A linear regression model may include a machine learning model. A linear regression model may be configured to map data of breath parameters, such as degree of relevancy, to one or more performance determination parameters. A linear regression model may be trained using a machine learning process. A linear regression model may map statistics such as, but not limited to, quality of breath parameters, category of breath parameters, and the like. In some embodiments, determining a performance determination of breath parameters may include using a performance determination classification model. A performance determination classification model may be configured to input collected data and cluster data to a centroid based on, but not limited to, frequency of appearance, linguistic indicators of quality, and the like. Centroids may include scores assigned to them such that quality of data and/or other classifications of breath parameters may each be assigned a score. In some embodiments performance determination classification model may include a K-means clustering model. In some embodiments, performance determination classification model may include a particle swarm optimization model. In some embodiments, determining the performance determination of a breath parameters may include using a fuzzy inference engine. A fuzzy inference engine may be configured to map one or more breath parameters data elements using fuzzy logic. In some embodiments, breath parameters may be arranged by a logic comparison program into performance determination arrangement. An "performance determination arrangement" as used in this disclosure is any grouping of data based on skill level and/or output score. This step may be implemented as described above in FIGS. 1-4. Membership function coefficients and/or constants as described above may be tuned according to classification and/or clustering algorithms. For instance, and without limitation, a clustering algorithm may determine a Gaussian or other distribution of questions about a centroid corresponding to a given competency level, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Further referring to FIG. 5, an inference engine may be implemented according to input and/or output membership functions and/or linguistic variables. For instance, a first linguistic variable may represent a first measurable value pertaining to breath parameters, such as a degree of influence of an element, while a second membership function may indicate a degree of in performance determination of a subject thereof, or another measurable value pertaining to breath parameters. Continuing the example, an output linguistic variable may represent, without limitation, a score value. An inference engine may combine rules, such as: "if respiration rate is 'low' and the plane movement is 'static', the operation of a sensing device is 'passive'"—the degree to which a given input function membership matches a given rule may be determined by a triangular norm or "T-norm" of the rule or output membership function with the input membership function, such as min (a, b), product of a and b, drastic product of a and b, Hamacher product of a and b, or the like, satisfying the rules of commutativity ($T(a, b)=T(b, a)$), monotonicity: ($T(a, b) \leq T(c, d)$ if $a \leq c$ and $b \leq d$), (associativity: $T(a, T(b, c))=T(T(a, b), c)$), and the requirement that the number 1 acts as an identity element. Combinations of rules ("and" or "or" combination of rule membership determinations) may be performed using any T-conorm, as represented by an inverted T symbol or "$\bot$" such as max(a, b), probabilistic sum of a and b ($a+b-a*b$), bounded sum, and/or drastic T-conorm; any T-conorm may be used that satisfies the properties of commutativity: $\bot(a, b)=\bot(b, a)$, monotonicity: $\bot(a, b) \leq \bot(c, d)$ if $a \leq c$ and $b \leq d$, associativity: $\bot(a, \bot(b, c))=\bot(\bot(a, b), c)$, and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

Further referring to FIG. 5, breath parameters to be used may be selected by user selection, and/or by selection of a distribution of output scores, such as 50% respiration rate, 40% oxygenation, and 10% VOC concentrations, or the like. Each performance determination categorization may be selected using an additional function such as in a performance determination as described above.

Figure 6:
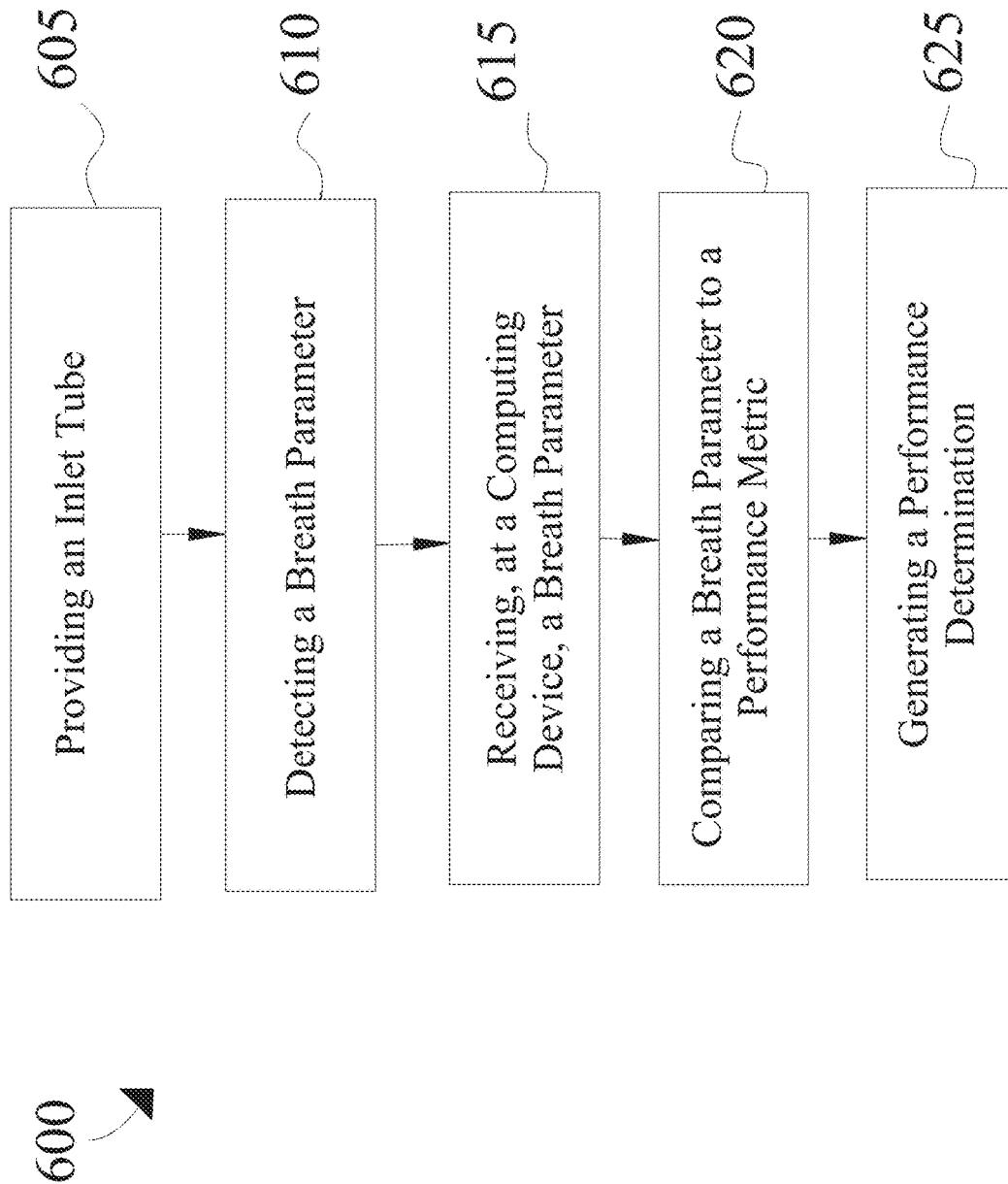
FIG. 6 is an exemplary embodiment of a flowchart of a method of using a human performance exhalation sensor.

Referring now to FIG. 6, a method 600 of using a human performance exhalation sensors is presented. At step 605, method 600 includes providing an inlet tube. An inlet tube may be provided to a user. An inlet tube may be configured to receive exhaled gas from a user. This step may be implemented, without limitation, as described above in FIGS. 1-4.

Still referring to FIG. 6, at step 610, method 600 includes detecting a breath parameter. A breath parameter may be detected through a sensing device of an inlet tube. A breath parameter may include, but is not limited to, respiration rates, oxygenation values, VOCs, and the like. This step may be implemented, without limitation, as described above in FIGS. 1-5.

Still referring to FIG. 6, at step 615, method 600 includes comparing a breath parameter to a performance metric. A performance metric may include, without limitation, a value and/or range of values corresponding to a competency of a completion of a task. This step may be implemented, without limitation, as described above in FIGS. 1-5.

Still referring to FIG. 6, at step 620, method 600 includes generating a performance determination. A performance determination may be generated as a function of a comparison of a breath parameter to a performance metric. This step may be implemented, without limitation, as described above in FIGS. 1-5.

Still referring to FIG. 6, at step 625, method 600 includes providing a feedback correlation to a user through a display device. This step may be implemented, without limitation, as described above in FIGS. 1-5.

Figure 7:
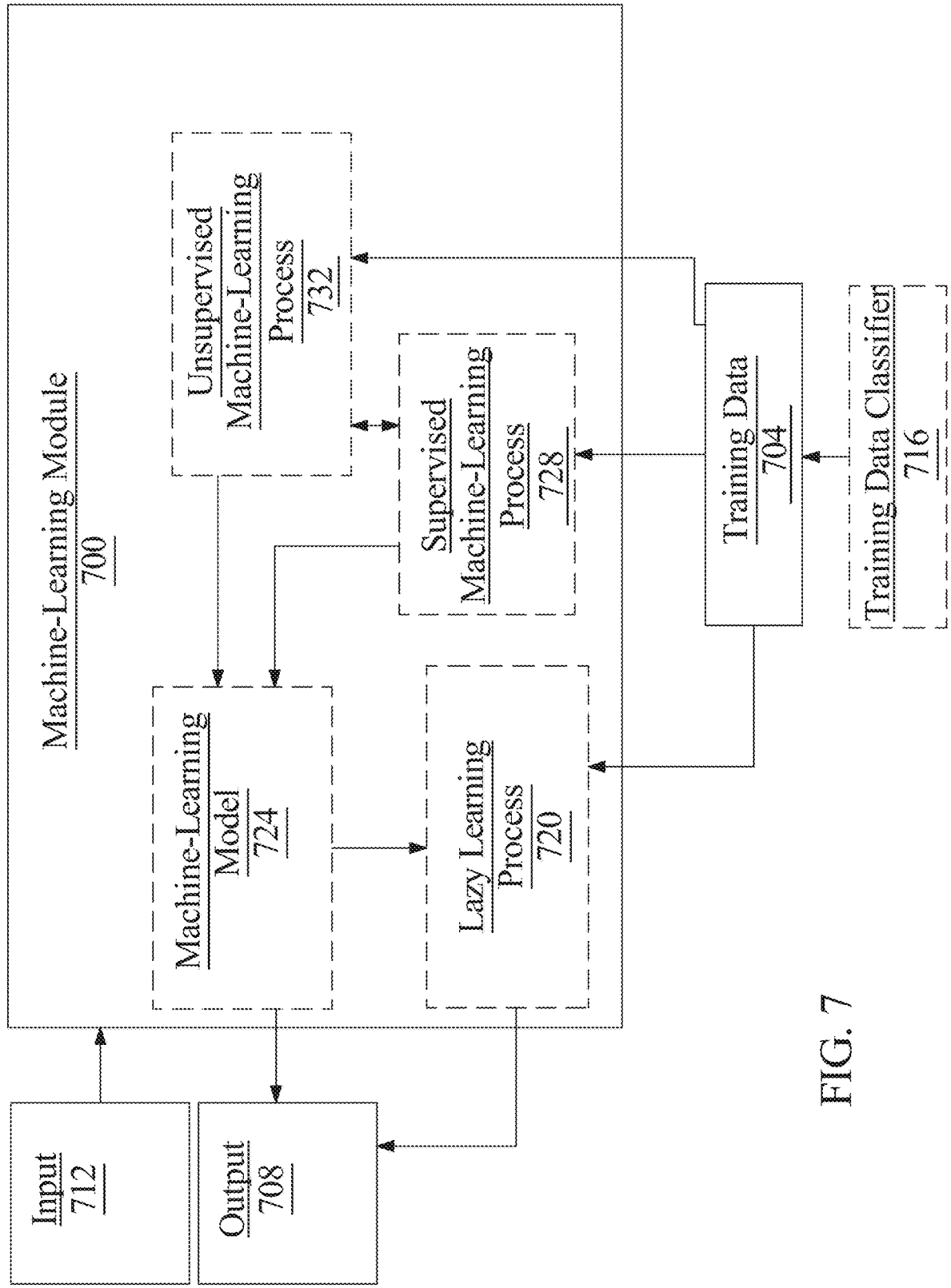
FIG. 7 is a diagram of an exemplary embodiment of a machine learning model.

Referring now to FIG. 7, an exemplary embodiment of a machine-learning module 700 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 704 to generate an algorithm that will be performed by a computing device/module to produce outputs 708 given data provided as inputs 712; this is in contrast to a non-machine learning software program where the commands to be executed are determined in advance by a user and written in a programming language.

Still referring to FIG. 7, "training data," as used herein, is data containing correlations that a machine-learning process may use to model relationships between two or more categories of data elements. For instance, and without limitation, training data 704 may include a plurality of data entries, each entry representing a set of data elements that were recorded, received, and/or generated together; data elements may be correlated by shared existence in a given data entry, by proximity in a given data entry, or the like. Multiple data entries in training data 704 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 704 according to various correlations; correlations may indicate causative and/or predictive links between categories of data elements, which may be modeled as relationships such as mathematical relationships by machine-learning processes as described in further detail below. Training data 704 may be formatted and/or organized by categories of data elements, for instance by associating data elements with one or more descriptors corresponding to categories of data elements. As a non-limiting example, training data 704 may include data entered in standardized forms by persons or processes, such that entry of a given data element in a given field in a form may be mapped to one or more descriptors of categories. Elements in training data 704 may be linked to descriptors of categories by tags, tokens, or other data elements; for instance, and without limitation, training data 704 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 7, training data 704 may include one or more elements that are not categorized; that is, training data 704 may not be formatted or contain descriptors for some elements of data. Machine-learning algorithms and/or other processes may sort training data 704 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 704 to be made applicable for two or more distinct machine-learning algorithms as described in further detail below. Training data 704 used by machine-learning module 700 may correlate any input data as described in this disclosure to any output data as described in this disclosure. As a non-limiting illustrative example inputs may include breath parameters and outputs may include one or more performance determinations.

Further referring to FIG. 7, training data may be filtered, sorted, and/or selected using one or more supervised and/or unsupervised machine-learning processes and/or models as described in further detail below; such models may include without limitation a training data classifier 716. Training data classifier 716 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 700 may generate a classifier using a classification algorithm, defined as a processes whereby a computing device and/or any module and/or component operating thereon derives a classifier from training data 704. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 716 may classify elements of training data to performance parameters, tasks, subtasks, biases, and the like.

Still referring to FIG. 7, machine-learning module 700 may be configured to perform a lazy-learning process 720 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 704. Heuristic may include selecting some number of highest-ranking associations and/or training data 704 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 7, machine-learning processes as described in this disclosure may be used to generate machine-learning models 724. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 724 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 724 may be generated by creating an artificial neural network, such as a convolutional neural network comprising an input layer of nodes, one or more intermediate layers, and an output layer of nodes. Connections between nodes may be created via the process of "training" the network, in which elements from a training data 704 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 7, machine-learning algorithms may include at least a supervised machine-learning process 728. At least a supervised machine-learning process 728, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include breath parameters as described above as inputs, performance determinations as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 704. Persons skilled in the art, upon reviewing the entirety of this disclosure, will be aware of various possible variations of at least a supervised machine-learning process 728 that may be used to determine relation between inputs and outputs. Supervised machine-learning processes may include classification algorithms as defined above.

Further referring to FIG. 7, machine learning processes may include at least an unsupervised machine-learning processes 732. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 7, machine-learning module 700 may be designed and configured to create a machine-learning model 724 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 7, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIRE-WIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for human performance exhalation sensing, comprising:
  a housing, wherein the housing comprises:
    an inlet tube configured to receive exhaled gas from an individual;
    a sensing device positioned within the inlet tube;
  at least a processor; and
  a memory communicatively connected to the at least a processor, the memory containing instructions configuring the at least a processor to:
    receive performance data related to at least a task assigned to the individual;
    generate a performance metric of the individual as a function of the performance data, wherein the performance metric comprises a performance parameter associated with the at least a task;
    generate a breath profile of the individual as a function of data collected from the exhaled gas;
    generate a performance determination of the individual as a function of the performance parameters and the breath profile by generating a performance determination machine learning model which comprises:
      receiving training data, wherein the training data correlates a plurality of breath parameter data and a plurality of performance data to a plurality of performance determination data;
      training, iteratively, the performance determination machine learning model using the training data, wherein training the performance determination machine learning model includes retraining the performance determination machine learning model with feedback from previous iterations of the performance determination machine learning model;
      generating the performance determination using the trained performance determination machine learning model; and
    alert the individual based on the generated performance determination.

2. The apparatus of claim 1, wherein the performance parameter comprises a parameter related to a biological performance of the individual.

3. The apparatus of claim 1, wherein the performance parameter comprises a physiological parameter.

4. The apparatus of claim 1, wherein generating the performance metric comprises:
  classifying the performance data into the performance parameter using a performance parameter classifier, wherein classifying the performance data to the performance parameter comprises:

classifying the at least a task into at least a task category associated with the performance parameter.

5. The apparatus of claim 1, wherein the breath profiles comprises a plurality of breath parameters.

6. The apparatus of claim 1, wherein generating the performance determination comprises tuning the performance determination as a function of the breath profile.

7. The apparatus of claim 1, wherein the performance determination comprises a performance score.

8. The apparatus of claim 1, wherein generating the performance determination comprises:
  determining a confidence metric associated with the performance determination using the performance determination machine learning model.

9. The apparatus of claim 1, wherein the memory further contains instructions configuring the at least a processor to:
  display the alert using a display device on an exterior surface of the housing to alert the individual.

10. A method of using a human performance exhalation sensor, comprising:
  providing an inlet tube to a user, wherein the inlet tube is configured to receive exhaled gas from an individual;
  receiving, by at least a processor communicatively connected to the sensing device, performance data related to at least a task assigned to the individual;
  generating a performance metric of the individual as a function of the performance data, wherein the performance metric comprises a performance parameter associated with the at least a task;
  generating, by the at least a processor, a breath profile of the individual as a function of data collected from the exhaled gas;
  generating, by the at least a processor, a performance determination as a function of the performance parameter and the breath profile by generating a performance determination machine learning model which comprises:
    receiving training data, wherein the training data correlates a plurality of breath parameter data and a plurality of performance data to a plurality of performance determination data;
    training, iteratively, the performance determination machine learning model using the training data, wherein training the performance determination machine learning model includes retraining the performance determination machine learning model with feedback from previous iterations of the performance determination machine learning model;
    generating the performance determination using the trained performance determination machine learning model; and
  alerting, by the at least a processor, the individual based on the generated performance determination.

11. The method of claim 10, wherein the performance parameter comprises a parameter related to a biological performance of the individual.

12. The method of claim 10, wherein the performance parameter comprises a physiological parameter.

13. The method of claim 10, wherein generating the performance metric comprises:
  classifying the performance data into the performance parameter using a performance parameter classifier, wherein classifying the performance data to the performance parameter comprises:
    classifying the at least a task into at least a task category associated with the performance parameter.

14. The method of claim 10, wherein the breath profiles comprises a plurality of breath parameters.

15. The apparatus of claim 1, wherein generating the performance determination comprises tuning the performance determination as a function of the breath profile.

16. The method of claim 10, wherein the performance determination comprises a performance score.

17. The method of claim 10, wherein generating the performance determination comprises:
  determining a confidence metric associated with the performance determination using the performance determination machine learning model.

18. The method of claim 10, wherein the memory further contains instructions configuring the at least a processor to:
  display the alert using a display device on an exterior surface of the housing to alert the individual.

* * * * *